United States Patent [19]
Kantorovich et al.

[11] Patent Number: 5,143,072
[45] Date of Patent: Sep. 1, 1992

[54] APPARATUS FOR DETERMINING THE MECHANICAL PROPERTIES OF A SOLID

[75] Inventors: Edward Kantorovich, Tel Aviv; Alex Rapoport, Rishon Lezion, both of Israel

[73] Assignee: Medicano Systems Ltd., Rishon Lezion, Israel

[21] Appl. No.: 708,776

[22] Filed: May 29, 1991

[30] Foreign Application Priority Data

Jun. 4, 1990 [IL] Israel ............................. 94616

[51] Int. Cl.$^5$ ............................................. A61B 8/00
[52] U.S. Cl. .......................... 128/660.02; 128/660.01; 73/597; 73/598; 73/599
[58] Field of Search .................. 128/660.01, 660.02, 128/660.07, 661.01, 661.03; 73/597, 598, 599

[56] References Cited

U.S. PATENT DOCUMENTS

| | | | |
|---|---|---|---|
| 3,127,950 | 4/1964 | Itria | 73/597 |
| 3,228,232 | 1/1966 | Proctor | 73/597 |
| 3,288,241 | 11/1966 | Bancroft et al. | 73/589 |
| 3,372,163 | 3/1968 | Tessandori | 546/49 |
| 3,512,400 | 5/1970 | Lynnworth | 73/597 |
| 3,720,098 | 3/1973 | Dixon | 73/597 |
| 3,847,141 | 11/1974 | Hoop | 128/660.01 |
| 4,361,154 | 11/1982 | Pratt, Jr. | 73/597 |
| 4,372,163 | 2/1983 | Tittmann et al. | 73/597 |
| 4,421,119 | 12/1983 | Pratt, Jr. | 73/597 |
| 4,566,459 | 1/1986 | Umemura et al. | 128/660.07 |
| 4,597,292 | 5/1986 | Fujii et al. | 73/599 |
| 4,640,132 | 2/1987 | Flora et al. | 73/602 |
| 4,752,917 | 6/1988 | Dechape | 73/597 |
| 4,774,959 | 10/1988 | Palmer et al. | 128/660.06 |
| 4,896,278 | 1/1990 | Grove | 73/598 |
| 4,913,157 | 4/1990 | Pratt, Jr. et al. | 128/661.03 |
| 4,926,870 | 5/1990 | Brandenburger | 128/660.01 |
| 4,930,511 | 5/1990 | Rossman et al. | 128/661.03 |
| 4,941,474 | 5/1990 | Pratt, Jr. | 128/661.01 |
| 4,976,267 | 12/1990 | Jeffcott et al. | 128/660.01 |
| 4,982,339 | 1/1991 | Insana et al. | 128/660.01 |
| 4,993,416 | 2/1991 | Ophir | 73/599 |
| 5,029,475 | 7/1991 | Kikuchi et al. | 128/661.03 |
| 5,038,615 | 8/1991 | Trulson et al. | 73/597 |
| 5,038,787 | 8/1991 | Antich et al. | 128/660.01 |
| 5,042,489 | 8/1991 | Wiener et al. | 128/661.03 |

FOREIGN PATENT DOCUMENTS

| | | | |
|---|---|---|---|
| 1159556 | 6/1985 | U.S.S.R. | 128/660.01 |
| 1172534 | 8/1985 | U.S.S.R. | 128/660.01 |
| 1175435 | 8/1985 | U.S.S.R. | 128/660.01 |
| 1308319 | 5/1987 | U.S.S.R. | 128/660.01 |
| 1342479 | 10/1987 | U.S.S.R. | 128/660.01 |
| 1420383 | 8/1988 | U.S.S.R. | 128/660.01 |

OTHER PUBLICATIONS

"Inspection, Processing and Manufacturing Control of Metal by Ultrasonic Methods", *Symposium on Ultrasonic Testing*, by C. H. Hastings and S. W. Carter, 52nd Annual Meeting of the American Society for Testing Materials, Jun. 28, 1949, pp. 16–47.

*Wave Motion in Elastic Solids*, by Karl F. Graff, published by the Clarendon Press, Oxford, England in 1975, p. 326.

"Osteoporotic Bone Fragility: Detection by Ultrasound Transmission Velocity", R. P. Heaney et al.; *JAMA*, vol. 261, No. 20, May 26, 1989, pp. 2986–2990.

"Measurement of the Velocity of Ultrasound in Human Cortical Bone in Vivo", M. A. Greenfield, et al., *Radiology*, vol. 138, Mar. 1981, pp. 701–710.

"Combined 2.25 MHz Ultrasound Velocity and Bone Mineral Density Measurements in the Equine Metacarpus and their In Vivi Applications", R. N. McCartney and L. B. Jeffcott, *Medical and Biological Engineering and Computation*, vol. 25, 1987, Nov. 1877, pp. 620–626.

*Primary Examiner*—Francis Jaworski
*Assistant Examiner*—George Manuel
*Attorney, Agent, or Firm*—Abelman Frayne & Schwab

[57] ABSTRACT

Apparatus for determining, through an interposed medium, the mechanical properties of a solid. The apparatus includes ultrasonic transmission apparatus for transmitting an ultrasonic wave through the interposed medium and the solid, wherein the solid has a surface, at least first and second ultrasonic receiver units, for receiving the ultrasonic wave, and apparatus for locating the receiver units such that a first receipt time of the ultrasonic wave from the surface to the first receiver unit is generally equivalent to a second receipt time from the surface to the second receiver unit.

34 Claims, 8 Drawing Sheets

APPARATUS FOR DETERMINING THE MECHANICAL PROPERTIES OF A SOLID

FIELD OF THE INVENTION

The present invention relates to instrumentation for non-destructive measurement of mechanical properties of materials generally and to instrumentation for non-invasive measurement of the mechanical properties of bone and bone quality.

BACKGROUND OF THE INVENTION

It is known in the art that the velocity of a sound wave in a material depends on the mechanical properties of the material. This is outlined by C. H. Hastings and S. W. Carter in an article entitled "Inspection, Processing and Manufacturing Control of Metal by Ultrasonic Methods", *Symposium on Ultrasonic Testing*. 52nd Annual Meeting of the American Society for Testing Materials, Jun. 28, 1949, pp. 16–47.

U.S. Pat. Nos. 3,720,098, 3,228,232, 3,288,241, 3,372,163, 3,127,950, 3,512,400, 4,640,132, 4,597,292 and 4,752,917 describe the state of the art of non-destructive testing.

A sound wave which reaches a semi-infinite solid at an angle will typically propagate through the solid as three waves, namely, the longitudinal, transverse and surface waves, wherein each wave has a different velocity. As described by Hastings and Carter, the velocities of the three waves are defined as follows:

$$V_L = \sqrt{\frac{E(1-\sigma)}{rho(1+\sigma)(1-2\sigma)}} \tag{1}$$

$$V_T = \sqrt{\frac{E}{2(1+\sigma)rho}} \tag{2}$$

$$V_S = \alpha V_T \tag{3a}$$

$$\alpha = \frac{0.87 + 1.12\sigma}{1+\sigma} \tag{3b}$$

where $V_L$, $V_T$, and $V_S$ are, respectively, the velocities of the longitudinal, transverse and Rayleigh surface waves, and E, $\sigma$ and rho are, respectively, the Young's Modulus, the Poisson's ratio of lateral contraction to longitudinal extension and the mass density of the material. Equation 3b is an imperical relationship as defined on page 326 of *Wave Motion in Elastic Solids*, by Karl F. Graff, published by the Clarendon Press, Oxford England in 1975.

In ultrasonic measurement of the condition of bone, typically only the velocity of the longitudinal wave is used. As defined in the article, "Osteoporotic Bone Fragility: Detection by Ultrasound Transmission Velocity," R. P. Heaney et al., *JAMA*, Vol. 261, No. 20, May 26, 1989, pp. 2986–2990, the Young's modulus of a bone E is given empirically as:

$$E = K \, (rho)^2 \tag{4a}$$

and the velocity of sound through the bone is a function of E, where the velocity of sound is typically the longitudinal velocity, as follows:

$$V_L = \sqrt{(E/rho)} = \sqrt{(K \cdot rho)} \tag{4b}$$

where K is a constant which incorporates a number of factors, such as spatial orientation of the bone structures, inherent properties of the bone material and fatigue damage. Thus, the velocity of a longitudinal wave is a function of the mass density and can be used as an indicator of the quality of bone.

The following articles also discuss ultrasonic measurement of bone condition both in vivo and in vitro.

"Measurement of the Velocity of Ultrasound in Human Cortical Bone In Vivo," M. A. Greenfield, et al., *Radiology*, Vol. 138, March 1981, pp. 701–710.

"Combined 2.25 MHz ultrasound velocity and bone mineral density measurements in the equine metacarpus and their in vivo applications," R. N. McCartney and L. B. Jeffcott, *Medical and Biological Engineering and Computation*, Vol. 25, 1987, Nov. 1877, pp. 620–626.

In order to perform in vivo ultrasonically measurements of the mechanical properties of bone, it is necessary to transmit an ultrasonic wave through the soft tissue surrounding the bone. Unfortunately, the thickness of the soft tissue varies along the length of the bone. This can affect the accuracy of the ultrasound propagation time measurement through the bone. In the abovementioned articles, the thickness of the soft tissue is either ignored or an attempt is made to cancel the effects of the soft tissue. In the articles describing in vitro experiments, the soft tissue is removed from the bone.

Russian patents 1,420,383, 1,308,319, 1,175,435, 1,324,479, 1,159,556 and 1,172,534 and U.S. Pat. Nos. 4,926,870, 4,361,154, 4,774,959, 4,421,119, 4,941,474, 3,847,141, 4,913,157 and 4,930,511 describe various systems for measuring the strength of bone based on the velocity $V_L$. These systems typically have one ultrasonic signal transmitter and at least one ultrasonic signal receiver.

Russian patents 1,420,383, 1,308,319 and 1,175,435 solve the problem of the unknown thickness of the soft tissue by assuming values for the thickness of the soft tissue in the area of the measurement or by assuming that the thickness variation is small over the distance between two ultrasonic signal receivers.

Russian patent 1,342,279 utilizes two receivers and a single transmitter and calculates an average group speed through the bone based on the known distance between the two receivers.

Russian patent 1,159,556 defines zones of a bone and the condition of a bone is determined by the difference between the maximum and minimum amplitude of the ultrasound signals measured. It would appear that this measurement is performed on an excised bone.

Russian patent 1,172,534 describes a system which compares the ultrasound signal of a healthy bone with that of an unhealthy bone and from the comparison, produces a diagnosis of the extent of disease in the unhealthy bone.

U.S. Pat. Nos. 4,926,870, 4,421,119 and 3,847,141 describe systems which places a receiver and a transmitter on opposite sides of a bone. U.S. Patent 4,926,870 also compares the resultant signal with a canonical waveform, thereby to identify the health of the bone.

U.S. Pat. Nos. 4,913,157, 4,774,959 and 4,941,474 describe systems which transmit an ultrasonic signal with a spectrum of frequencies.

U.S. Pat. No. 4,930,511 describes a system is placed around a standard inanimate homogeneous material of known acoustic properties before it is placed around a bone.

SUMMARY OF THE INVENTION

The present invention ultrasonically measures mechanical properties of a hard material wherein the ultrasonic signal travels from a transmitter, through a thickness of an interposed medium and through a hard material to be tested, such as a solid. The ultrasonic wave propagates through the hard material as three waves, the longitudinal, transverse and surface waves. From the solid, the ultrasonic wave travels through a second thickness to a first receiver and through a third thickness to a second receiver located a defined distance from the first receiver.

There is therefore provided, in accordance with an embodiment of the present invention, apparatus for determining, through an interposed medium, the mechanical properties of a solid. The apparatus includes ultrasonic transmission apparatus for transmitting an ultrasonic wave through the interposed medium and the solid, wherein the solid has a surface, at least first and second ultrasonic receiver units, for receiving the ultrasonic wave, and apparatus for locating the receiver units such that a first receipt time of the ultrasonic wave from the surface to the first receiver unit is generally equivalent to a second receipt time from the surface to the second receiver unit.

Additionally, in accordance with an embodiment of the present invention, the apparatus for locating adjusts the locations of the receiver units such that the first and second receipt times are generally equivalent. The apparatus for locating also includes apparatus for determining the first and the second receipt times.

Furthermore, in accordance with an embodiment of the present invention, the apparatus for determining includes apparatus for pulsing the transmission apparatus thereby to transmit an ultrasonic wave when the first and second receipt times are generally identical.

Still further, in accordance with an embodiment of the present invention, the solid is in vivo bone. Alternatively, the solid is selected from the group of metal, plastics and wood.

Moreover, in accordance with an embodiment of the present invention, the velocity of the ultrasonic wave through the interposed medium is less than the velocity of the ultrasonic wave through the solid.

Additionally, in accordance with an embodiment of the present invention, the first and second ultrasonic receiver units are placed onto a surface of the interposed medium generally without any coupling medium.

Further, in accordance with an embodiment of the present invention, the apparatus for locating include a rocker unit for rockingly pressing the receiver units into the interposed medium. The rocker unit typically includes an acoustically insulating unit.

Still further, in accordance with an embodiment of the present invention, the ultrasonic wave is transmitted in a wide band pattern and wherein the ultrasonic wave generates longitudinal, surface and transverse waves in the solid.

Moreover, in accordance with an embodiment of the present invention, the apparatus includes processing apparatus for processing signals from the receiver apparatus and for identifying a receipt time of the longitudinal wave. The processing apparatus includes apparatus for identifying receipt times of the surface and transverse waves.

Additionally, in accordance with an embodiment of the present invention, the processing apparatus includes apparatus for determining the mechanical properties from at least the receipt time for the longitudinal wave. Alternatively or in addition, the processing apparatus includes apparatus for determining the mechanical properties from the receipt times of the surface and transverse waves.

Further, in accordance with an embodiment of the present invention, the transmission apparatus transmits the ultrasonic wave within a generally small range of a predetermined angle.

Still further, in accordance with an embodiment of the present invention, a transmission surface of the transmission apparatus and effective receiving locations of the receiving apparatus are generally coplanar.

Moreover, in accordance with an embodiment of the present invention, the apparatus is characterized in that generally no knowledge of properties of the interposed medium are necessary.

There is also provided, in accordance with an embodiment of the present invention, a method for determining, through an interposed medium, the mechanical properties of a solid. The method includes the steps of transmitting an ultrasonic wave through the interposed medium and the solid, wherein the solid has a surface, receiving the ultrasonic wave with at least first and second ultrasonic receiver units, and locating the receiver units such that a first receipt time of the ultrasonic wave from the surface to the first receiver unit is generally equivalent to a second receipt time from the surface to the second receiver unit.

Additionally, in accordance with an embodiment of the present invention, the step of locating includes the step of adjusting the locations of the receiver units such that the first and second receipt times are generally equivalent.

Further, in accordance with an embodiment of the present invention, the step of locating includes the step of determining the first and the second receipt times.

Still further, in accordance with an embodiment of the present invention, the step of determining includes the step of pulsing the transmission apparatus thereby to transmit an ultrasonic wave when the first and second receipt times are generally identical.

Moreover, in accordance with an embodiment of the present invention, the solid is in vivo bone. Alternatively, the solid is selected from the group of metal,,- plastics and wood.

Additionally, in accordance with an embodiment of the present invention, the velocity of the ultrasonic wave through the interposed medium is less than the velocity of the ultrasonic wave through the solid.

Furthermore, in accordance with an embodiment of the present invention, the first and second ultrasonic receiver units are placed onto a surface of the interposed medium generally without any coupling medium.

Still further, in accordance with an embodiment of the present invention, the step of locating include a rocker unit for rockingly pressing the receiver units into the interposed medium.

Additionally, in accordance with an embodiment of the present invention, the method includes the step of transmitting the ultrasonic wave in a wide band pattern and wherein the ultrasonic wave generates longitudinal, surface and transverse waves in the solid.

Moreover, in accordance with an embodiment of the present invention, the method includes the steps of processing signals from the receiver apparatus and identifying a receipt time of the longitudinal wave.

Finally, in accordance with an embodiment of the present invention, the step of processing includes the step of identifying receipt times of the surface and transverse waves. The step of processing preferably includes the step of determining the mechanical properties from at least the receipt time for the longitudinal wave. Alternatively, or in addition, the step of processing includes the step of determining the mechanical properties from the receipt times of the surface and transverse waves.

BRIEF DESCRIPTION OF THE DRAWINGS

The present invention will be understood and appreciated more fully from the following detailed description taken in conjunction with the drawings in which:

FIGS. 8A-8D are graphical illustrations indicating the output signals from elements of the signal processor of FIG. 7; and FIGS. 9A-9C are schematic illustrations of transmitters useful in the embodiments of FIGS. 3 and 5.

DETAILED DESCRIPTION OF PRESENT INVENTION

Figure 1:
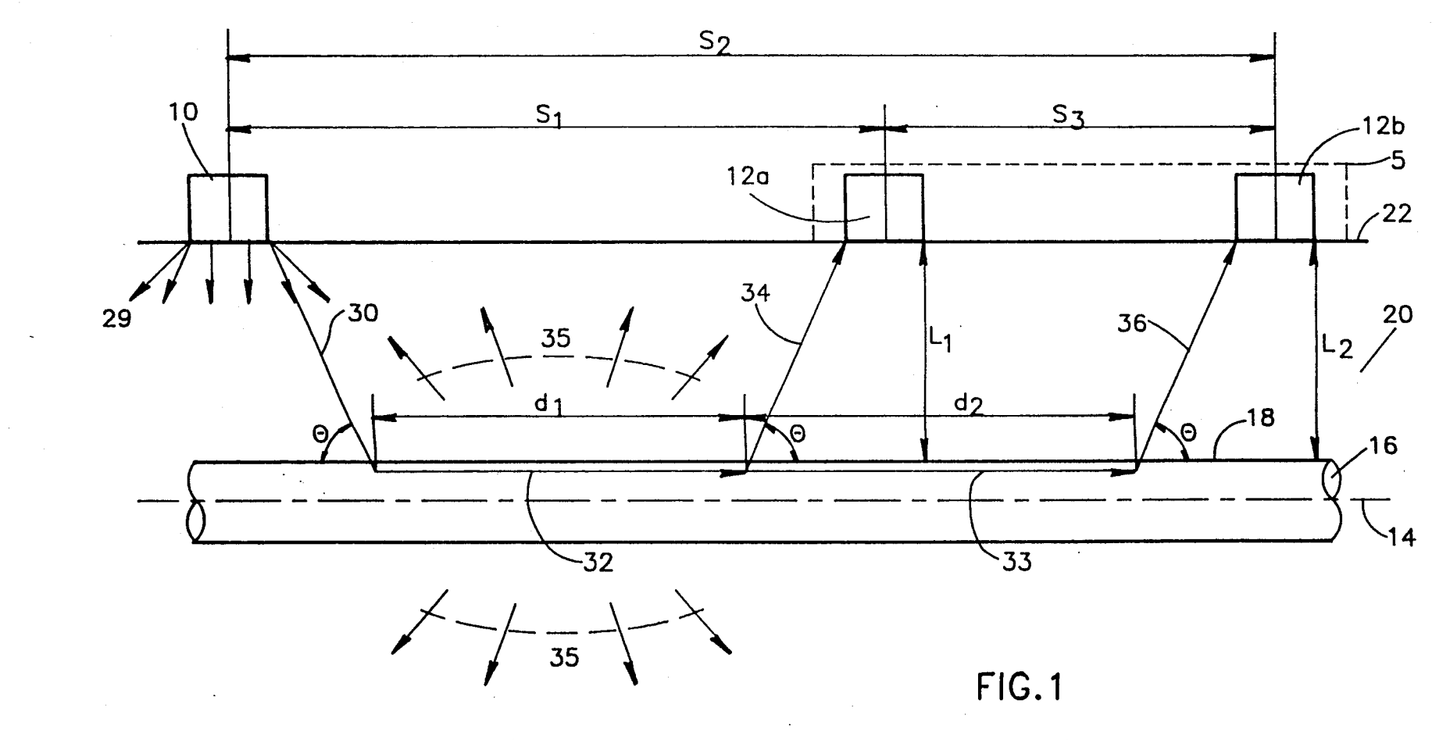
FIG. 1 is a schematic illustration of a method of ultrasonically measuring mechanical properties of materials operative with the present invention.

Reference is now made to FIG. 1 which schematically illustrates a method of ultrasonically measuring mechanical properties of a hard material, such as a solid 16, and apparatus which implements the method constructed and operative in accordance with the present invention. The apparatus comprises an ultrasonic transmitter 10, such as an ultrasonic transducer made of piezoelectric ceramics, typically capable of transmitting ultrasonic signals at frequencies in the range of 20 KHz to 10 MHz, and a receiver unit 5 for receiving the transmitted signals. Unit 5 typically comprises at least two ultrasonic receivers 12 such as ultrasonic transducers made of piezoelectric ceramics.

The unit 5 and transmitter 10 are placed generally in the direction of a long axis 14 of solid 16 and preferably parallel to a surface 18 of solid 16. Solid 16 is typically a metal whose mechanical properties, such as Young's Modulus (E), density (rho) and Poisson's ratio ($\sigma$), are to be measured. It can also be skeletal bone.

Along surface 18 of the solid 16 is typically an interposed medium 20, such as a gel or water for a metal solid 16 or such as soft tissue typically surrounding skeletal bone. The transmitter 10 and receivers 12 are typically placed on a top surface 22 of the interposed medium 20 wherein the receivers 12 are located at distances $s_1$ and $s_2$ from transmitter 10. In accordance with the present invention, thicknesses $L_1$ and $L_2$ of the interposed medium 20 under each of receivers 12 are preferably generally equivalent.

In accordance with an alternative embodiment of the present invention, the interposed medium 20 is not utilized and the transmitter 10 and receivers 12 are placed directly on surface 18 of solid 16.

The transmitter 10 typically transmits an ultrasonic wave 29 which propagates through the interposed medium 20 as a longitudinal wave until it reaches surface 18. A portion of wave 29, marked by arrow 30, reaches surface 18 at an angle Θ to surface 18 where Θ is the Brewster Angle. As is known in the art, the wave 29 generates in solid 16 three waves, the longitudinal, transverse and surface waves, schematically marked by arrow 32. As is known in the art, if the hard material is not a solid 16, only the longitudinal wave will be propagated.

The three waves propagate through solid 16 and generate longitudinal waves 35 in interposed medium 20 to be received by receivers 12.

Portions of waves 35, marked by arrows 34 and 36, propagate through interposed medium 20 at angle θ with respect to surface 18. As is known in the art, the path marked by arrows 30, 32 and 34 is the shortest path an ultrasonic wave can take to reach a first one of receivers 12, marked 12a. The shortest path to reach a second one of receivers 12, marked 12b, is marked by arrows 30, 32, 33 and 36. Thus, a wave propagating along the paths marked by arrows 30, 32, 34 or 30, 32, 33 and 36 will be received first; other waves propagating along other paths will be received later.

The Brewster angle Θ is calculated as follows:

$$\theta = \arccos(V_L'/V_L) \qquad (5)$$

where $V_L'$ is the velocity of a longitudinal wave in interposed medium 20 and $V_L$ is the velocity of a longitudinal wave in hard material 16. For soft tissue, $V_L'$ is on average 1540 m/s and for bone, $V_L$ is on average 3500 m/s, producing a Brewster angle θ of roughly 65°.

The first ultrasonic wave to reach receiver 12a is a longitudinal wave which leaves solid 16 at the Brewster Angle θ after traveling through solid 16 for a distance $d_1$. The first ultrasonic wave to reach receiver 12b is a longitudinal wave which travels through solid 16 for a distance $d_1 + d_2$.

Figure 2A:
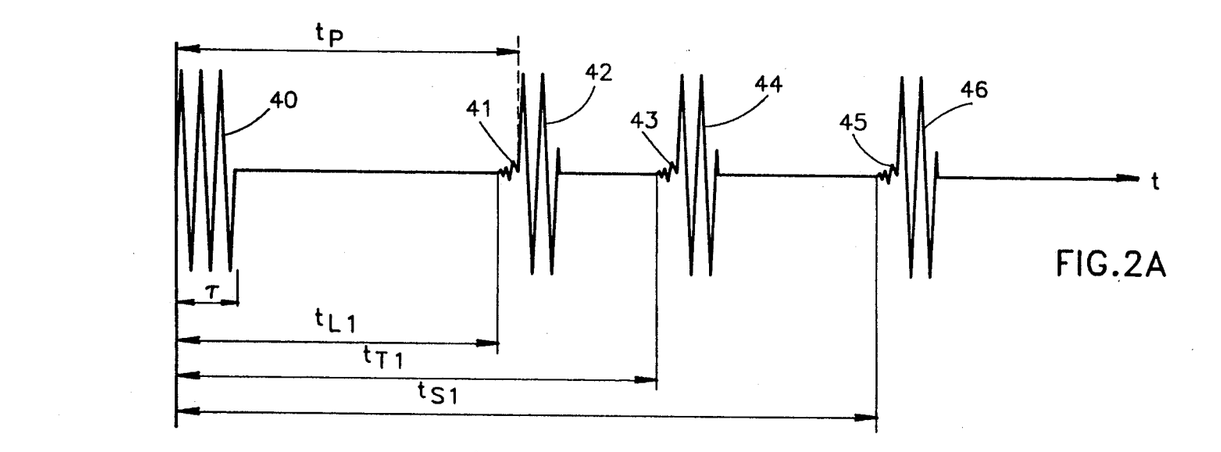
FIGS. 2A and 2B are graphic illustrations of ultrasonic signals transmitted and received by ultrasonic transducers using the method of FIG. 1.
Figure 2B:
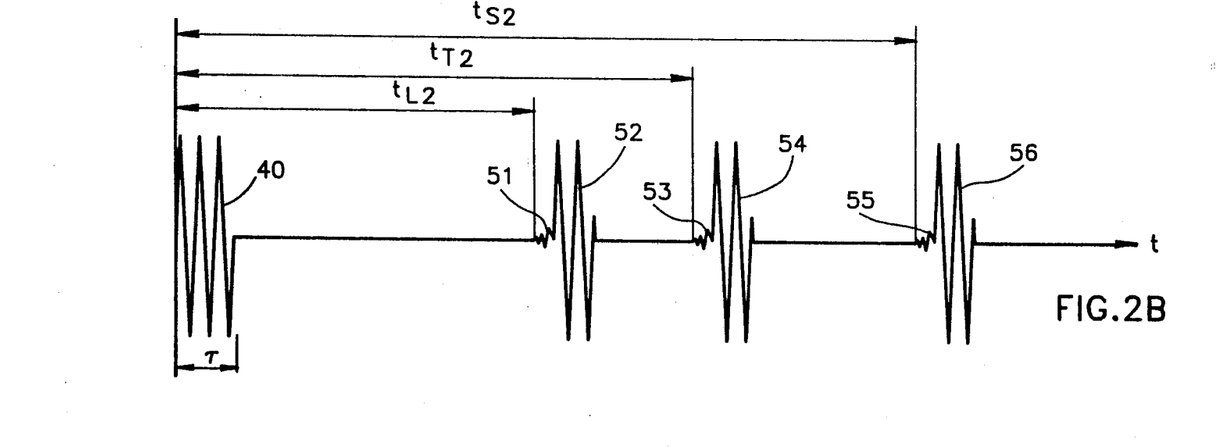

It will be appreciated that the three waves do not reach a receiver 12 at the same time due to their different velocities. This is illustrated in FIGS. 2A and 2B, to which reference is now briefly made. FIG. 2A illustrates a signal 40, representing the ultrasonic wave transmitted by transmitter 10, and signals 42, 44 and 46 which are received by receiver 12a and represent the longitudinal, transverse and surface waves, respectively.

Signal 40 is produced for a time tau, where tau is typically fairly short, so as to enable a separation between the longitudinal, transverse and surface waves. For example, 5 cycles of a 1 MHz signal will produce a tau of 5 microseconds.

Signals 42, 44 and 46 comprise low energy portions 41, 43 and 45, respectively, corresponding to the first waves to reach receivers 12 which typically have much less energy compared to the later signals. In accordance with the present invention and in contrast to the prior art, propogation times $t_{L1}$, $t_{T1}$ and $t_{S1}$ are measured from the initiation of signal 40 (i.e. the beginning of transmission of ultrasonic wave 29) to the moment the first waves reach receivers 12. The prior art measures a propagation time $t_p$ measured from the initiation of signal 40 to the moment signal 42 reaches a significant amplitude. Propagation time $t_p$ measures the time of propagation of a reflected signal, rather than one propagated through solid 16.

As is known in the art, the larger the distance between the transmitter 10 and a receiver 12, the longer are the times $t_{L1}$, $t_{T1}$, $t_{S1}$ and the more separated are the signals 42, 44 and 46. The size of the distance $d_1$ necessary to produce a separation among the signals 42, 44 and 46 depends on the mechanical properties of the solid 16 and for bone are typically at least 5 cm.

It will be appreciated that the minimum value for $s_1$ depends on the thicknesses $L_1$ and $L_2$; the bigger $L_1$ and $L_2$ are, the bigger $s_1$ has to be to ensure that $d_1$ is greater than 0. In other words, there has to be some propagation through the solid 16. It will also be appreciated that $d_2$ has to be large enough to achieve accurate measurements and small enough to ensure that the signals 52, 54 and 56 have not overly decreased in power due to absorption of the signal energy by solid 16. Typically, $d_2$ is a few cm.

FIG. 2B is similar to FIG. 2A and illustrates signals 52, 54 and 56 received by receiver 12b. Signals 52, 54 and 56 respectively comprise low energy portions 51, 53 and 55. It will be appreciated that each of low energy portions 51, 53 and 55 are received slightly later than each of low energy portions 41, 43 and 45, respectively. The propagation times are marked $t_{L2}$, $t_{T2}$ and $t_{S2}$.

The velocity of propagation of each of the longitudinal, transverse and surface waves can be calculated by taking a known distance, such as the distance from receiver 12a and 12b, $s_3 = s_2 - s_1$, and dividing by the propagation time through that distance. The propagation time through $s_3$ is calculated for the longitudinal wave as follows.

The propagation time $t_{L1}$ is a combination of propagation times $t_{30}$, $t_{32}$ and $t_{34}$ for the waves marked by arrows 30, 32 and 34, respectively, and the propagation time $t_{L2}$ is a combination of propagation times $t_{30}$, $t_{32}$, $t_{33}$ and $t_{36}$ for the waves marked by arrows 30, 32, 33 and 36, respectively. Written mathematically, this becomes equations 6a and 6b.

$$t_{L1} = t_{30} + t_{32} + t_{34} \quad (6a)$$

$$t_{L2} = t_{30} + t_{32} + t_{33} + t_{36} \quad (6b)$$

If the thicknesses $L_1$ and $L_2$ of the interposed medium 20 under receivers 12 are generally equivalent and because the angle to both receivers 12 is 0, the propagation time through the interposed medium 20 to the receivers 12 will be equivalent, or $$t_{34} = t_{36} \quad (7)$$

Taking the difference between equations 6b and 6a and including equation 7 produces $$t_{L2} - t_{L1} = t_{33} \quad (8)$$

Simple geometry states that if the thicknesses $L_1$ and $L_2$ are generally equivalent and since the angle of propagation of the waves marked by arrows 34 and 36 is equivalent, the distances $d_2$ and $s_3$ will be generally equivalent. Therefore, $$V_L = s_3 / (t_{L2} - t_{L1}) \quad (9)$$

Similarly, $$V_T = s_3 / (t_{T2} - t_{T1}) \quad (10)$$

$$V_S = s_3 / (t_{S1} - t_{S1}) \quad (11)$$

Thus, equations 1-2 can be solved to produce the Poisson's ratio $\sigma$ and a ratio $E/\rho$ as follows.

$$\sigma = \frac{B - 2}{2(B - 1)} \quad (12)$$

$$\frac{E}{\rho} = \frac{V_L^2(3B - 4)}{B(B - 1)} \quad (13)$$

or $$\frac{E}{\rho} = 2V_T^2 \left[ 1 + \frac{B - 2}{2(B - 1)} \right] \quad (14)$$

where $$B = (V_L/V_T)^2 \quad (15)$$

Figure 3:
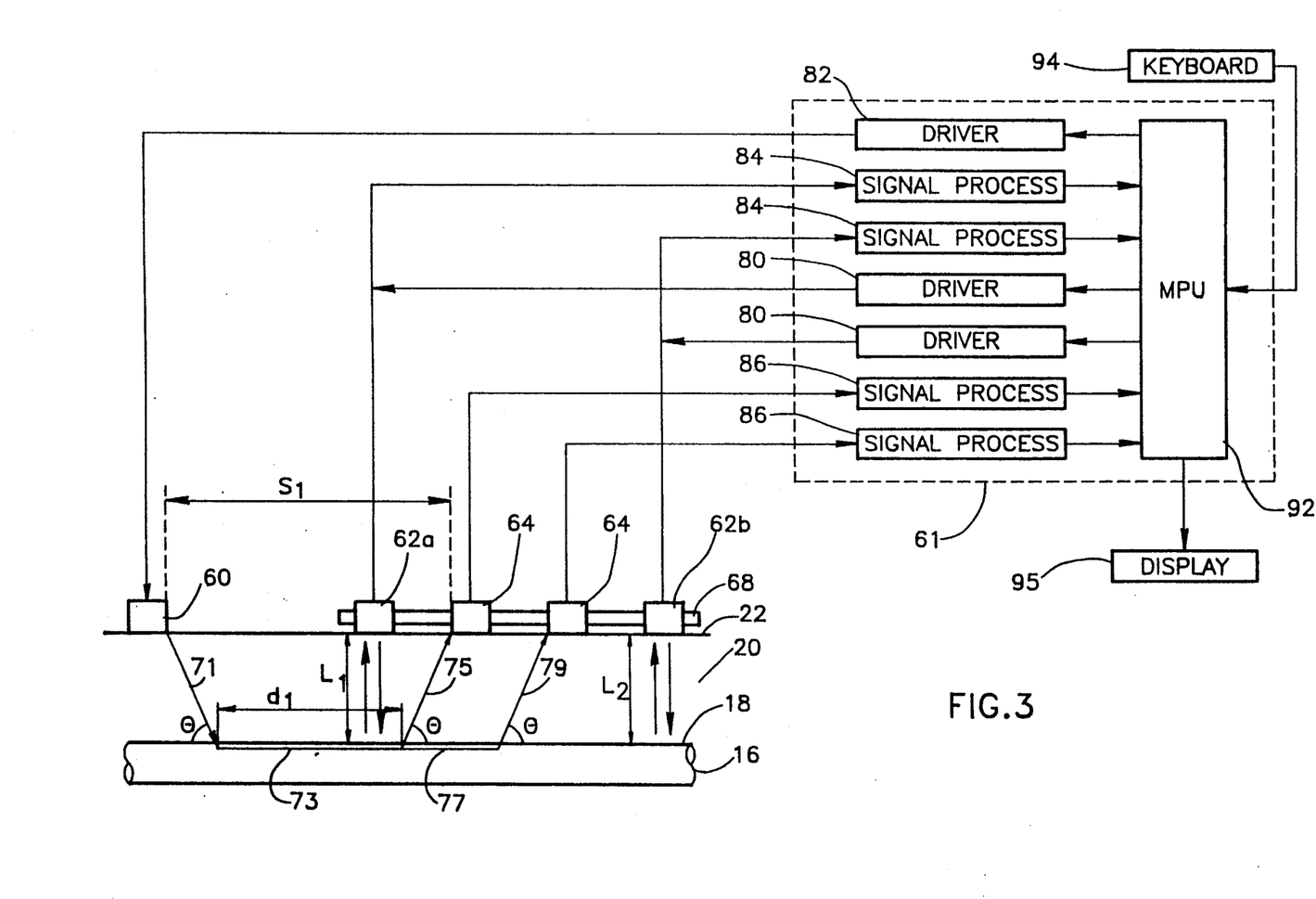
FIG. 3 is a part block diagram, part schematic illustration of in vivo ultrasonic apparatus for mechanical property measurement utilizing the method of FIG. 1.

Reference is now made to FIG. 3 which illustrates apparatus for in vivo measuring of the mechanical properties of a solid, such as bone, which is surrounded by an interposed medium, such as soft tissue, of unknown and non-constant thickness, constructed and operative in accordance with a preferred embodiment of the present invention.

Figure 9:
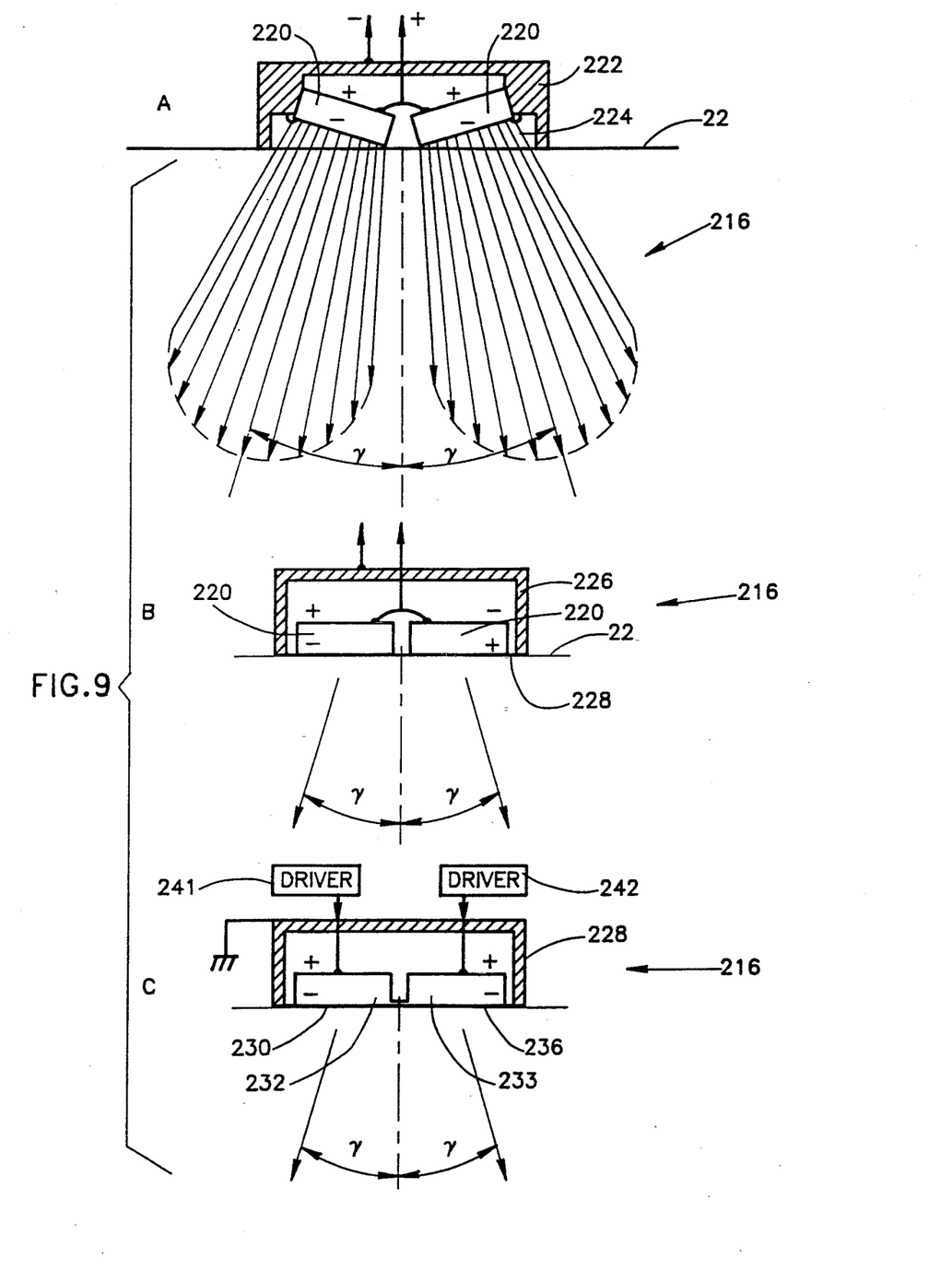

The apparatus for in vivo measuring typically comprises an ultrasonic transmitter 60, typically transmitting in the range 20 KHz–10 MHz, for transmitting an ultrasonic wave 71, at least two ultrasonic transmitter-receivers 62 transmitting typically in the range 20 KHz–10 MHz, for estimating the thickness of the interposed medium 20 surrounding a solid 16, a plurality of ultrasonic receivers 64 for receiving the ultrasonic signal transmitted by the transmitter 60 and a processing unit 61. Preferred embodiments for transmitter 60 and receivers 64 are shown in FIGS. 9A–9C.

The two transmitter-receivers 62 and the receivers 64 are typically combined in a unit located such that there is a distance $s_1$ between the transmitter 60 and a first receiver 64. Typically, the receivers 64 are located between the transmitter-receivers 62. Thus, if the thickness of the interposed medium 20 surrounding the solid 16 is generally equivalent under the transmitter-receivers 62, it is equivalent under the plurality of receivers 64.

In accordance with a preferred embodiment of the present invention, the two transmitter-receivers 62 are operative to transmit an ultrasonic wave in a direction generally perpendicular to the surface 22 of the interposed medium 20 and to receive the reflection of the transmitted wave from surface 18. The transmitter-receivers 62 and the receivers 64 are pressed into the interposed medium 20 so as to change their locations with respect to the solid 16 until the received signals have propagated in the interposed medium 20 for the same length of time.

Additionally, transmitter-receivers 62 are operative to estimate the thickness $L_1$. The estimate of $L_1$ is useful in estimating the distance $s_1$, useful in defining the placement of transmitter 60. Through geometric considerations, $s_1$ is approximated as follows:

$$s_1 {}^{18} d_1 + 2L_1/\tan\theta \quad (16)$$

Since, as mentioned hereinabove, the distance $d_1$ must be greater than 0, $s_1$ is calculated to be larger then $2L_1/\tan\theta$, typically by 30-40%. Alternatively, $s_1$ can be a fixed distance from the receivers 64.

Figure 4:
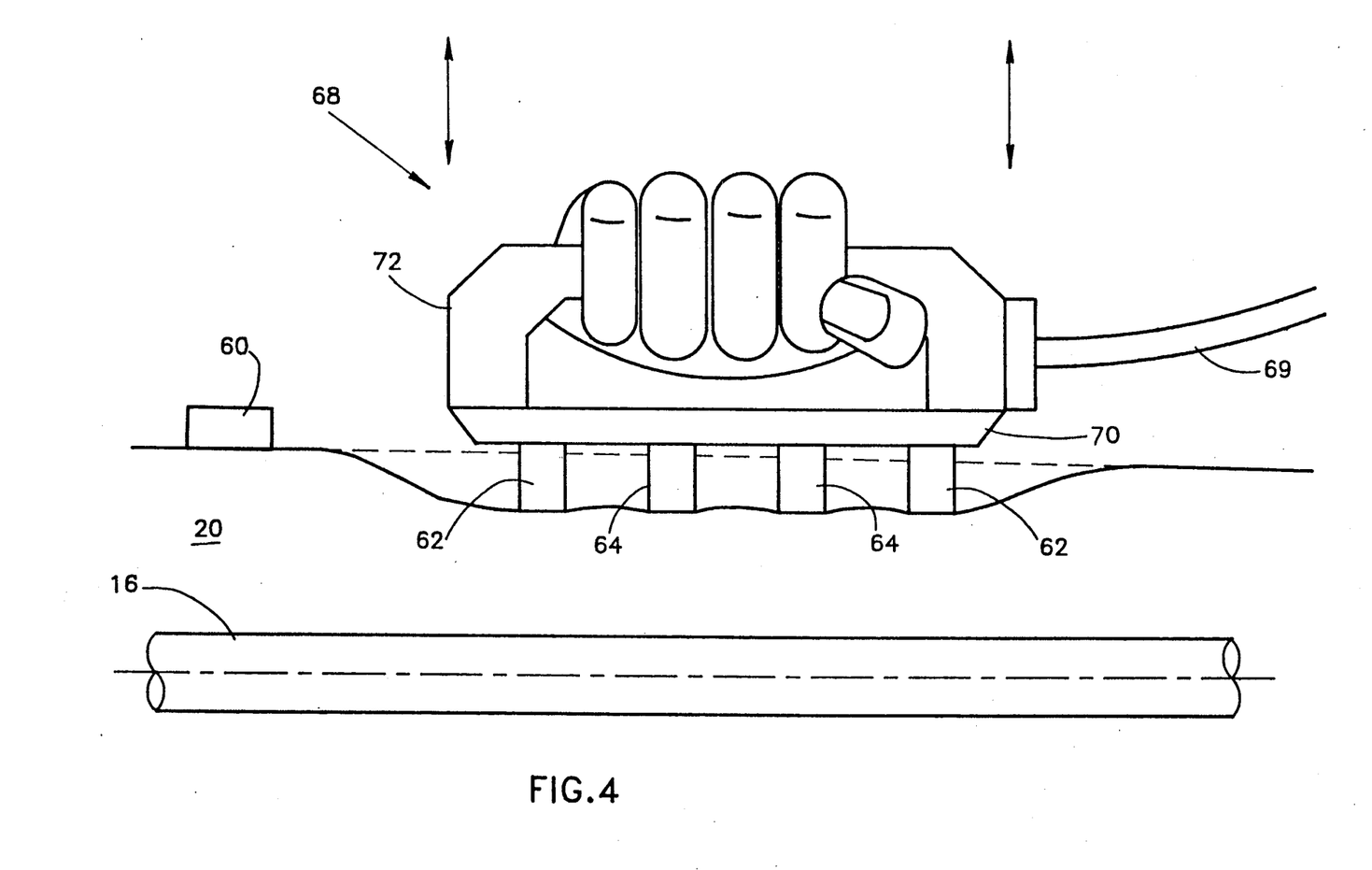
FIG. 4 is a pictorial illustration of apparatus for ensuring that ultrasonic transducers are parallel to a surface of a material to be measured useful in the apparatus of FIG. 3.

To effect the change in location of the transmitter-receivers 62 and the receivers 64, the elements 62 and 64 are combined together in a single rockable unit 68 as shown in FIG. 4 to which reference is now briefly made. The elements 62 and 64 are held together in a unit 70 to which is attached a rocking unit 72, such as a handle, to rockingly press the elements 62 and 64 into the interposed medium 20. By "rockingly press" it is meant that the rocking unit 72 is slowly rocked from side to side while pressing into the interposed medium 20. Attached to the rockable unit 68 are cables 69 for connecting the rockable unit 68 to the processing unit 61.

It will be appreciated that rockable unit 68 can be any suitable unit, whether manually or automatically operated.

It will also be appreciated that rockable unit 68 can be slidingly moved along surface 22 while measurements are performed, as described hereinbelow. Accordingly, measurements along the solid 16 can be taken, giving an operator an indication of locations of changes or discontinuities in the quality of the material of solid 16.

While the rockable unit 68 is being rocked, the transmitter-receivers 62 continually transmit and receive ultrasonic waves. The received signals are sent to the processing unit 61 which continually measures receipt times of the two received signals, where a receipt time is the time to measure the thicknesses $L_1$ and $L_2$ When the difference between the receipt times of the two received signals is generally zero, indicating that the thickness of the interposed medium 20 between the two transmitter-receivers 60 and the solid 16 is generally equivalent, the processing unit 61 causes the transmitter 60 to transmit an ultrasonic wave, marked by arrow 71.

Receivers 64 receive the ultrasonic wave after it has passed through the interposed medium 20 and the solid 16, as shown by arrows 73, 75, 77 and 79. Processing unit 61 receives the received signals, calculates at least $t_{L1}$ and $t_{L2}$, and from them, calculates $V_L$ which is correlated to the mechanical properties of bone, as defined in Equation 4b. Additionally, processing unit 61 can calculate the ratio E/rho and $\sigma$ from equations 12-15.

It will be appreciated that the transmission and reception of the ultrasonic signals occurs within typically 200 microseconds so that any changes due to rocking of the rockable unit 70 have generally no effect on the thickness of the interposed medium 20 under the receivers 64 during the measurement.

Reference is made back to FIG. 3. The processing unit 61 comprises drivers 80 and 82 for driving ultrasonic transmitter-receivers 62 and transmitter 60, respectively, and signal processor units 84 and 86 for processing the received signals from transmitter-receivers 62 and from receivers 64, respectively.

Processing unit 61 additionally comprises a Main Processing Unit (MPU) 92, such as a microcontroller, for controlling the apparatus through sending driving signals to drivers 80 and 82 and receiving and processing signals from signal processor units 84 and 86. MPU 92 additionally interfaces with an operator of the apparatus of the present invention through a keyboard 94 and a display 95.

If $s_1$ is not fixed, at the beginning of a measurement, it is approximated as follows. Rockable unit 68 is rockingly pressed into interposed medium 20 while MPU 92 pulses transmitter-receivers 62 and receives signals from them via signal processor units 84 using the larger threshold level $T_2$. When delta—t, the time difference between the receipt times of the received signals, is generally zero, MPU 92 calculates the time $t_{tr}$, between the transmission and receipt of each signal sent by and reflected to each transmitter-receiver 62. By multiplying $t_{tr}$ by the known average velocity of sound in soft tissue, MPU 92 calculates $L_1$ which is then used in equation 17 for defining the distance $s_1$.

To take a measurement, the rockable unit 68 is again rockingly pressed into interposed medium 20 while MPU 92 alternates, at a high frequency, between pulsing one transmitter-receiver, marked 62a, and the other transmitter-receiver, marked 62b. It receives the processed signals from signal processor units 84 and calculates a time difference delta—t between the receipt times of the received signals from transmitter-receivers 62. When delta—t is generally zero, MPU 92 pulses driver 82 to produce the ultrasonic wave marked by arrow 71 and stops pulsing drivers 80.

The ultrasonic wave produces ultrasonic waves, marked by arrows 75 and 79, which are received by receivers 64. The received signal is processed by signal processors 86 and the output is sent to MPU 92 for evaluation of at least the time difference $t_{L2} - t_{L1}$ and for calculation of at least the velocity $V_L$, in accordance with equation 9.

It will be appreciated that the apparatus of the present invention is operative to calculate $V_S$ and $V_T$ also, utilizing the method outlined hereinabove with respect to FIGS. 1 and 2. From the calculation of $V_L$, $V_S$ and $V_T$, the ratio E/rho and $\sigma$ can be calculated. It will be noted, however, that the calculation of $V_L$ is necessary for comparing the results of the apparatus of the present invention with results of other prior art devices.

Reference is now made to FIGS. 7 and 8A–8D which respectively illustrate the elements of signal processor unit 84 or 86 and their operation.

Figures 7, 8:
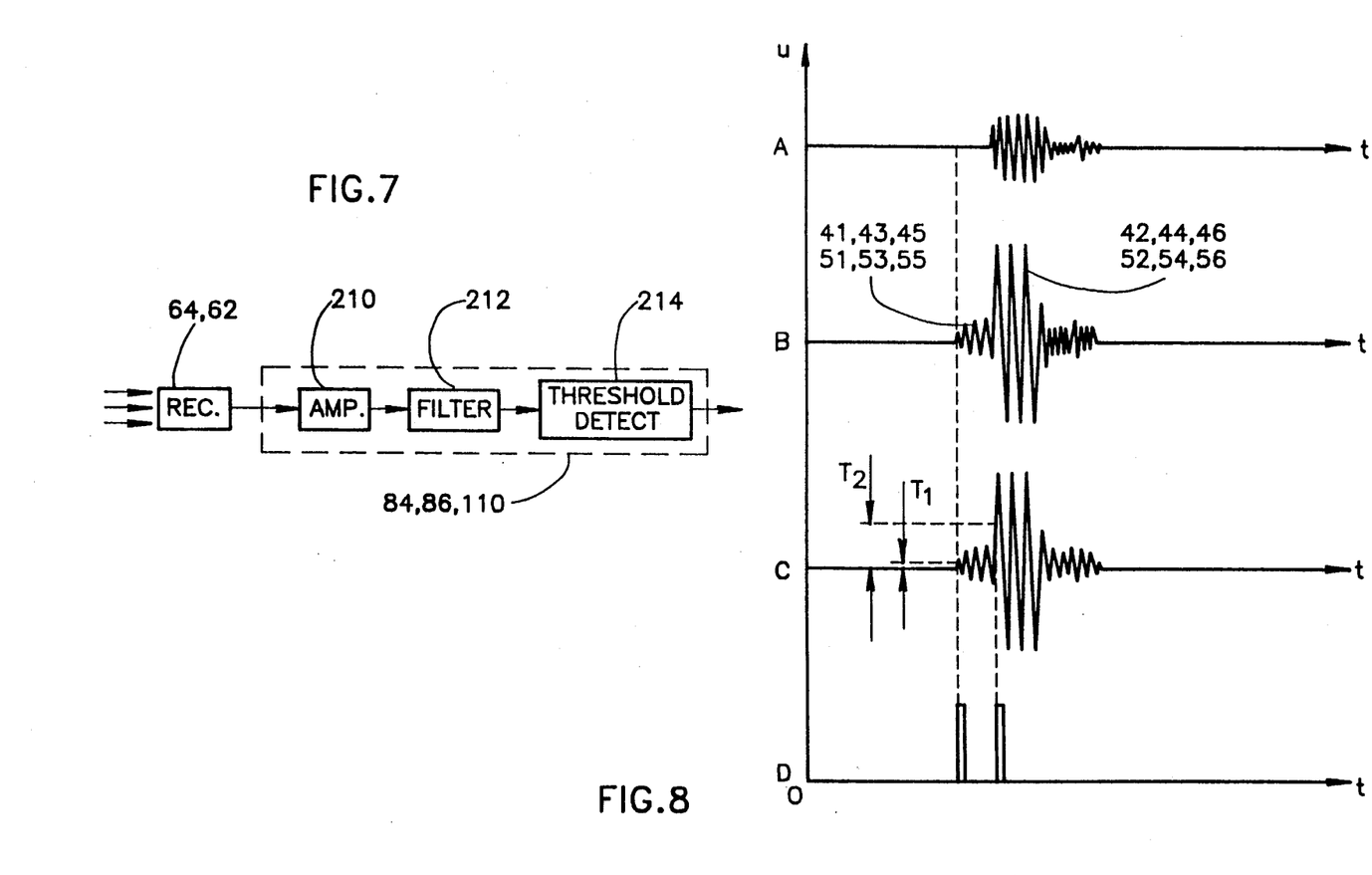
FIG. 7 is a block diagram illustration of signal processors useful in the embodiments of FIGS. 3 and 5.

In order to measure the moment the first waves reach receivers 64, signal processor unit 84 or 86 comprises an automatic gain control amplifier 210 of high sensitivity and low noise/signal ratio for exponentially amplifying signals 42 and 52 so as to measure the initiation of portions 41 and 51 and to compensate for the typical exponential attenuation of ultrasonic signals. The output of the amplifier 210 is shown in FIG. 8B for an input signal 42 of FIG. 8A where signal 42 comprises a low energy portion 41.

Signal processor unit 84 or 86 additionally comprises a band pass filter 212 for filtering out all signals not in the range of frequencies transmitted by transmitter 60, thereby to reduce noise in the received signal produced by the amplification or otherwise. Its output is shown in FIG. 8C for the input signal of FIG. 8B.

Furthermore, each signal processor unit 84 and 86 comprises a threshold detector 214 for identifying the initiation of either signals 42 and 52 or portions 41 and 51, respectively. Thus, threshold levels $t_1$ and $T_2$, shown in FIG. 8C, are defined. $T_1$ identifies the portions 41 and 51 and $T_2$ identifies the signals 42 and 52. The output of threshold detector 214 is shown in FIG. 8D for an input signal of FIG. 8C.

Figure 5:
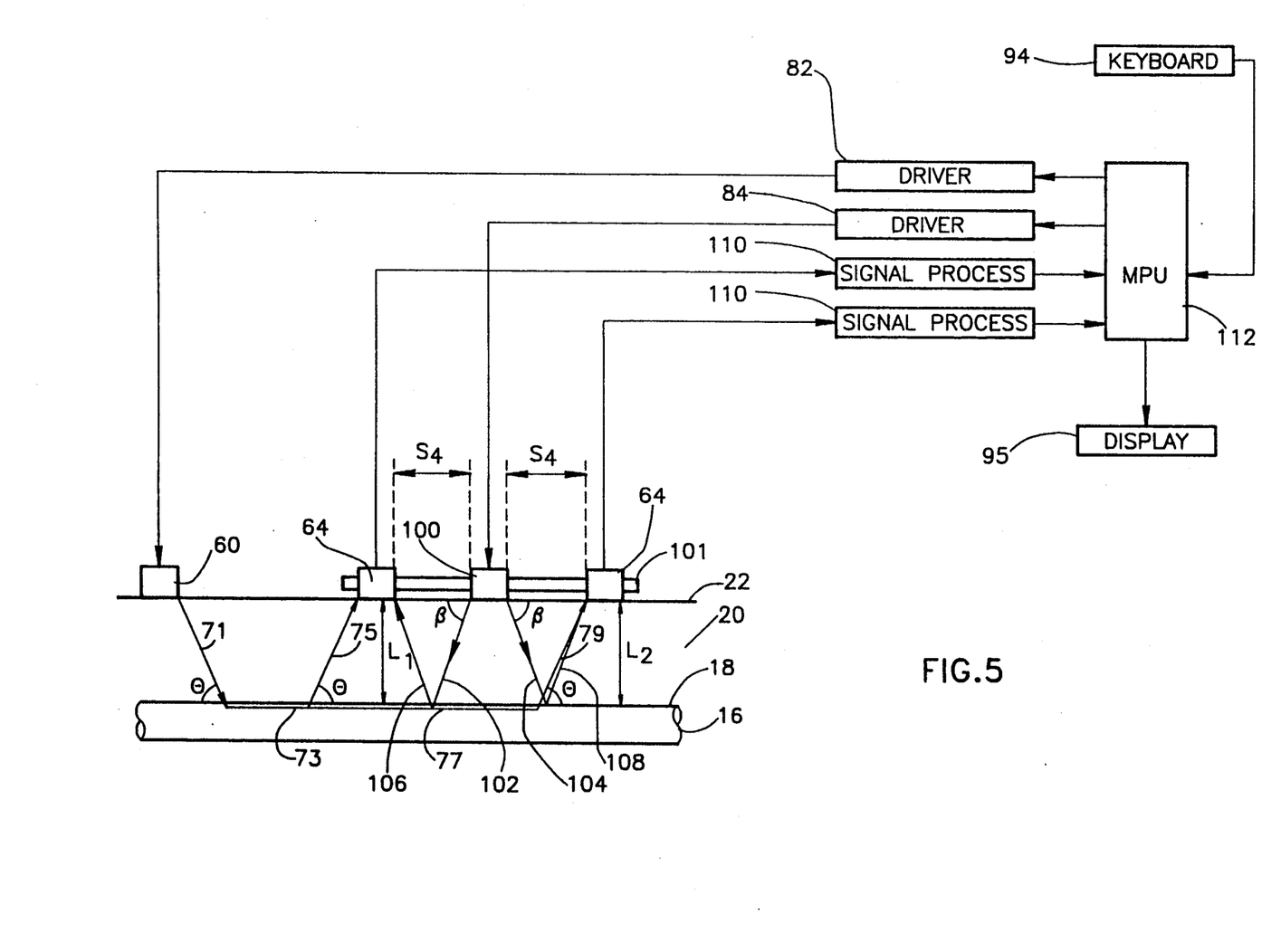
FIG. 5 is a part block diagram, part schematic illustration of an alternative embodiment of the apparatus of FIG. 3.

Reference is now made to FIG. 5 which illustrates an alternative embodiment of the apparatus of FIG. 3. In this embodiment, the two transmitter-receivers 62 are replaced by a single transmitter 100, described in more detail hereinbelow with reference to FIGS. 9A–9C, located exactly equidistant between an even plurality of receivers 64. Transmitter 100 and at least two receivers 64 are connected together via an acoustically insulated unit 101. Unit 101 is shown in detail in FIGS. 6A–6C.

Transmitter 100 transmits at least two ultrasonic waves at a general direction having a non-zero angle gamma (FIGS. 9A–9D) with respect to a perpendicular axis of surface 22 (not shown). A portion of the two waves, marked 102 and 104 in FIG. 5 and having an angle $\beta$ as shown, are reflected from solid 16 to receivers 64 as waves 106 and 108. The angle $\beta$ is unknown and depends on the thicknesses $L_1$ and $L_2$.

Receivers 64 receive reflections 106 and 108, from the surface 18, and send the received signal to signal processors 110, similar to signal processors 84 and 86 of the embodiment of FIG. 3, for processing with both threshold level $T_1$ and $T_2$. The processed signal is then sent to a MPU 112, similar to MPU 92 of the embodiment of FIG. 3.

If $s_1$ is not fixed, at the beginning of a measurement, it is approximated as follows. Unit 101 is rockingly pressed into interposed medium 20 while MPU 112 pulses transmitter 100 and receives signals from receivers 64 via signal processor units 110 using the larger threshold level $T_2$. When delta—t, the time difference between the receipt times of the received signals, is generally zero, MPU 112 calculates the time $t_{tr}$, similar to time $t_p$ of FIG. 2A, between the transmission and receipt of each signal sent by transmitter 100 and received by receivers 64.

Once $t_{tr}$ is calculated, the thickness $L_1$ is approximated as follows:

$$L_1 = \sqrt{[(V_L' \cdot t_{tr}/2)^2 - (s_4/2)^2]} \quad (17)$$

where $s_4$ is the distance between transmitter 100 and a receiver 64. Since, as mentioned hereinabove, the distance $d_1$ must be greater than 0, $s_1$ is calculated, in accordance with equation 16, to be larger then $2L_1/\tan\theta$, typically by 30–40%.

During a measurement, unit 101 is again rockingly pressed into interposed medium 20 while MPU 112 pulses transmitter 100 and receives signals from receivers 64 via signal processor units 110, using the larger threshold level $T_2$. When delta—t is generally zero, MPU 112 pulses driver 82 to produce the ultrasonic wave marked by arrow 71 and stops pulsing driver 84.

The ultrasonic wave produces ultrasonic waves, marked by arrows 75 and 79, which are received by receivers 64. The received signal is processed by signal processors 110, using threshold level $T_1$, and the output is sent to MPU 112 for evaluation of at least the time difference $t_{L2} - t_{L1}$ and for calculation of at least the velocity $V_L$, in accordance with equation 9.

Figure 6:
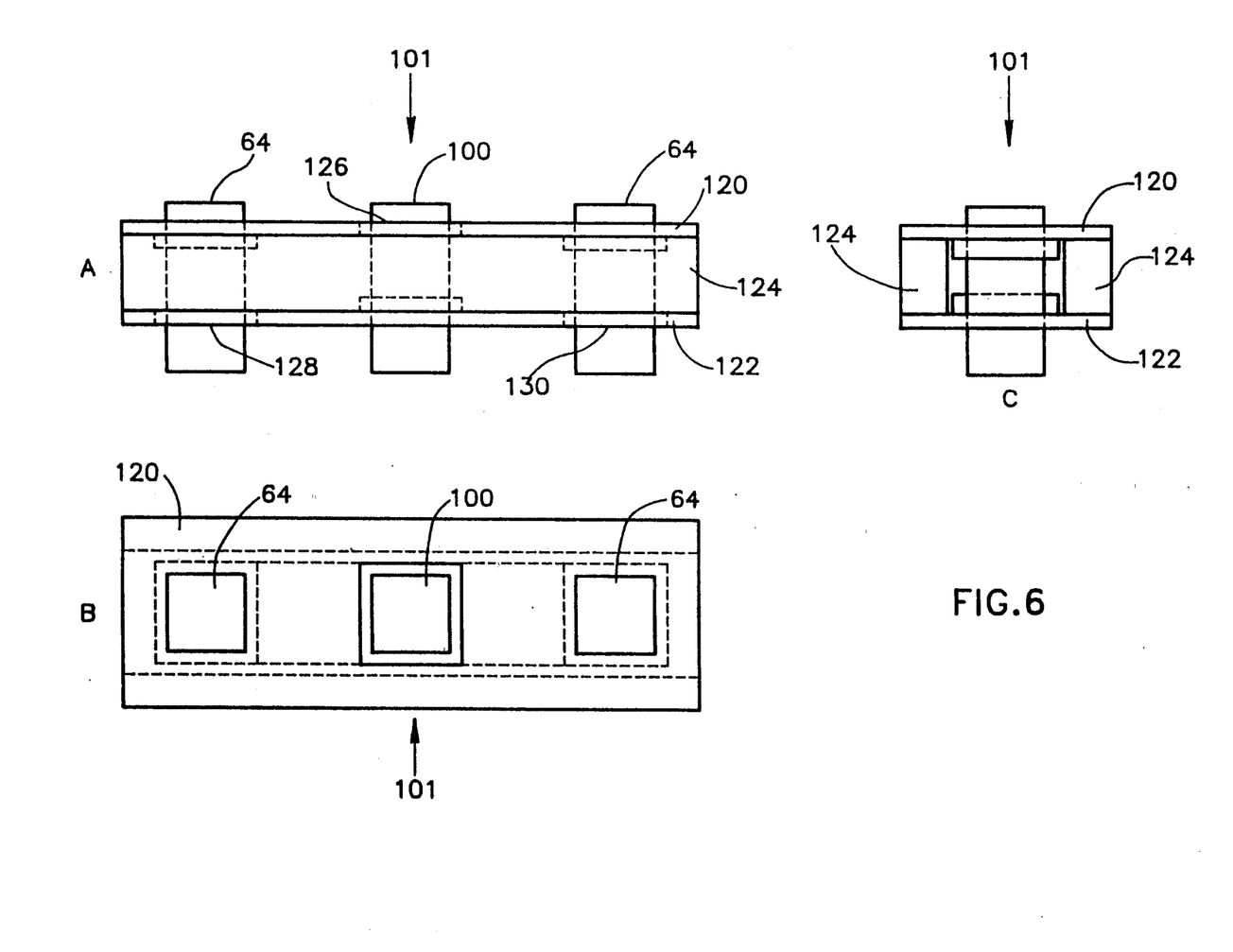
FIG. 6 is a schematic illustration of an acoustically insulating element useful in the apparatus of FIG. 5.

Reference is now made to FIGS. 6A–6C which are side, top and end view illustrations of the acoustically insulated unit 101. The transducers 64 and 100 of FIG. 5 are enclosed in two rigid frames 120 and 122, typically of metal, between which is an acoustically absorbant material 124, such as elastic rubber. Receivers 64 are attached to frame 120 and transmitter 100 is attached to frame 122, wherein frame 120 has a hole 126 in which transmitter 120 sits and frame 122 has holes 128 and 130 in which sit receivers 64.

The material 124 is operative to absorb ultrasonic waves which are transmitted by transmitter 100 such that receivers 64 do not receive such waves before receipt of the ultrasonic waves propagated through the solid 16. Frames 120 and 122 are operative to provide a firm shape to material 124. Each frame only holds one type of ultrasonic transducer; for example, frame 120 holds only receivers 64.

Unit 101 is necessary to ensure that the ultrasonic wave transmitted by transmitter 100 is received by receivers 64 only after having propagated through solid 16. Without the acoustic insulation provided by unit 101, it is possible that the first signals received by receivers 64 are those from wave which propagated through frames 120 and 122.

Reference is now made to FIGS. 9A–9C which illustrate preferred embodiments of an ultrasonic transceiver 216 operative as transmitters 60 and 100 and receivers 64. Transceiver 216 is operative to transmit an ultrasonic wave 71 at an angle gamma and to receive energy which arrives generally in that direction thereby increasing the amount of energy available in low energy portions 41 and 51.

Ultrasonic transceiver 216 is configured to produce ultrasonic waves in two directions, marked by angles gamma, and generally no wave in the direction perpendicular to the surface 22 on which transceiver 216 stands. Typically, gamma $= 90 - \theta$.

In FIG. 9A, transceiver 216 comprises two standard ultrasonic transducers 220 having positive and negative terminals, denoted by $+$ and $-$ signs, respectively, whose positive terminals are connected together. Transducers 220 are housed in a housing 222 comprising two angled portions 224 on which sit transducers 220. The angled portions 224 are typically comprised of an acoustically transmissive material, such as gel. In this embodiment, the negative terminals are connected to ground and the positive terminals are connected to a driver.

A second embodiment of transceiver 216 is shown in FIG. 9B. As in the previous embodiment, transceiver 216 comprises two standard transducers 220 enclosed in a housing, labeled 226. In this embodiment, the positive terminal of one transducer 220 is connected to the negative terminal of the other, and vice versa. As is known in the art, this produces waves having opposite phases; thus, only the waves generally at an angle gamma are produced. One positive-negative terminal pair is placed on an electrode 228 which is typically placed along surface 22. The other positive-negative terminal pair, which is connected to a driver, is located inside housing 226. The housing 226 is connected to ground.

FIG. 9C illustrates a third embodiment of transceiver 216 which is housed in a housing 228 and is comprised of a single ultrasonic transducer 230 which is at least partially cut into two sections 232 and 233. The negative terminals of sections 232 and 233 are typically attached to an electrode 236 and the positive terminals of sections 232 and 233 are connected to opposite polarity drivers 240 and 241 such that section 232 receives a positive signal at the same time that section 233 receives a negative signal, and vice versa.

It will be appreciated that what has been described herein is merely illustrative of the method and apparatus of the present invention. Other methods of achieving the same goal are included in the present invention. For example, an alternative method for defining $s_1$ is as follows.

In FIG. 2A, signal 42 is typically produced by ultrasonic waves reflecting from the surface 18 of solid 16 and portion 41 is produced by waves propagating a distance $d_1$ through the solid 16. Thus, if there is a difference between the receipt time $t_{L1}$ of portion 41 and the receipt time $t_p$ of signal 42 then $d_1$ is greater than 0 as required. Measurement of $t_{L1}$ and $t_p$ merely requires that signal processors 86 and 100 have the two threshold levels $T_1$ and $T_2$.

It will be appreciated that the apparatus of the present invention is operative for thicknesses of an interposing medium 20 which are not equivalent, although the results are less accurate. Referring once again to FIG. 1, if the receipt times $t_{L1}$ and $t_{L2}$ differ by the measured value delta—t, then equations 6-8 are rewritten as follows into equations 18-20:

$$t_{L1} = t_{30} + t_{32} + t_{34} \quad (18a)$$

$$t_{L2} = t_{30} + t_{32} + t_{33} + t_{36} \quad (18b)$$

where $$t_{34} = t_{36} + \text{delta}-t \quad (19)$$

and delta—t might be positive or negative. Thus, $$t_{L2} - t_{L1} = t_{33} + \text{delta}-t \quad (20)$$

Since, due to geometric considerations, if $L_1$ is not equivalent to $L_2$ then $d_2$ is not necessarily equivalent to $s_3$. However, $$L_1 = L_2 + \text{delta}-L = L_2 + (\text{delta}-t)(V_L') \quad (21)$$

and therefore, $$d_2 = \sqrt{(s_3^2 - (\text{delta}-L))} \quad (22)$$

and $$V_L = d_2/(t_{L2} - t_{L1}) \quad (23)$$

It will further be appreciated that the apparatus of the present invention is operative without an interposing medium 20. For such a situation, unit 5 (FIG. 1) comprises only one receiver 12a and the equations 9-11 are:

$$V_L = s_1/t_{L1} \quad (24)$$

$$V_T = s_1/t_{T1} \quad (25)$$

$$V_S = s_1/t_{S1} \quad (26)$$

It will be appreciated by persons skilled in the art that the present invention is not limited to what has been particularly shown and described hereinabove. Rather the scope of the present invention is defined only by the claims which follow:

We claim:

1. Apparatus for determining, through an interposed medium, the mechanical properties of a solid having a surface, the apparatus comprising:
   ultrasonic transmission means located in a first location for transmitting ultrasonic waves through said interposed medium and through said solid and generally parallel to said surface;
   at least one ultrasonic receiver unit located in each of second and third locations for receiving said ultrasonic waves, wherein said first, second and third locations are colinear along said surface;
   means for locating said at least one ultrasonic receiver unit such that a first receipt time of an ultrasonic wave from said surface to said at least one ultrasonic receiver unit at said second location is generally equivalent to a second receipt time from said surface to said at least one ultrasonic receiver unit at said third location; and
   means for calculating said mechanical properties from ultrasonic waves transmitted by said ultrasonic transmission means once said first and second receipt times are generally equivalent.

2. Apparatus according to claim 1 and wherein said means for locating adjusts the locations of said receiver units such that said first and second receipt times are generally equivalent.

3. Apparatus according to claim 2 and wherein said means for locating includes means for determining said first and said second receipt times.

4. Apparatus according to claim 3 and wherein said means for determining includes means for pulsing said transmission means thereby to transmit ultrasonic waves when said first and second receipt times are generally equivalent.

5. Apparatus according to claim 2 and wherein said means for locating include a rocker unit for rockingly pressing said receiver units into said interposed medium.

6. Apparatus according to claim 5 and wherein said rocker unit comprises an acoustically insulating unit.

7. Apparatus according to claim 1 and wherein said solid is in vivo bone.

8. Apparatus according to claim 1 and wherein said solid is selected from the group of metal, plastics and wood.

9. Apparatus according to claim 1 and wherein the velocity of said ultrasonic waves through said interposed medium is less than the velocity of said ultrasonic wave through said solid.

10. Apparatus according to claim 1 and wherein said at least one ultrasonic receiver unit is placed onto a surface of said interposed medium generally without any coupling medium.

11. Apparatus according to claim 1 wherein said ultrasonic transmission means includes means for transmitting aid ultrasonic waves within a wide angle and wherein said ultrasonic waves generate longitudinal, surface and transverse waves in said solid.

12. Apparatus according to claim 11 and including processing means for processing signals from said at least one ultrasonic receiver unit and for identifying a receipt time of said longitudinal wave.

13. Apparatus according to claim 12 and wherein said processing means includes means for identifying receipt times of said surface and transverse waves.

14. Apparatus according to claim 13 and wherein said processing means includes means for determining said mechanical properties from said receipt times of said surface and transverse waves.

15. Apparatus according to claim 12 and wherein said processing means includes means for determining said mechanical properties from at least said receipt time for said longitudinal wave.

16. Apparatus according to claim 1 and wherein said transmission means transmits said ultrasonic wave within a generally small range of a predetermined angle.

17. Apparatus according to claim 1 and wherein a transmission surface of said transmission means and effective receiving locations of said receiving means are generally coplanar.

18. Apparatus for determining, through an interposed medium, the mechanical properties of a solid, the apparatus comprising:
ultrasonic transmission means for transmitting an ultrasonic wave through said interposed medium and said solid, wherein said solid has a surface;
at least first and second ultrasonic receiver units, for receiving said ultrasonic wave; and
means for locating said ultrasonic receiver units including a rocker unit for rockingly pressing said ultrasonic receiver units into said interposed medium such that a first receipt time of said ultrasonic wave from said surface to said first ultrasonic receiver unit is generally equivalent to a second receipt time from said surface to said second ultrasonic receiver unit,
wherein said means for locating adjusts the locations of said receiver units such that said first and second receipt times are generally equivalent.

19. Apparatus for determining, through an interposed medium, the mechanical properties of a solid, the apparatus comprising:
ultrasonic transmission means for transmitting an ultrasonic wave through said interposed medium and said solid, wherein said solid has a surface;
at least first and second ultrasonic receiver units, for receiving said ultrasonic wave; and
means for locating said ultrasonic receiver units including a rocker unit for rockingly pressing said ultrasonic receiver units into said interposed medium such that a first receipt time of said ultrasonic wave from said surface to said first ultrasonic receiver unit is generally equivalent to a second receipt time from said surface to said second ultrasonic receiver unit,
wherein said means for locating adjusts the locations of said receiver units such that said first and second receipt times are generally equivalent, and
wherein said rocker unit comprises an acoustically insulating unit.

20. A method for determining, through an interposed medium, the mechanical properties of a solid having a surface, the method comprising the steps of:
transmitting ultrasonic waves through said interposed medium and through said solid and generally parallel to said surface from a first location;
receiving said ultrasonic waves with at least one ultrasonic receiver unit, located in each of second and third locations, wherein said first, second and third locations are colinear along said surface;
locating said at least one ultrasonic receiver unit such that a first receipt time of an ultrasonic wave from said surface to said at least one ultrasonic receiver unit at said second location is generally equivalent to a second receipt time from said surface to said at least one ultrasonic receiver unit at said third location, and
calculating said mechanical properties from ultrasonic waves transmitted by said ultrasonic transmission means once said first and second receipt times are generally equivalent.

21. Method according to claim 19 and wherein said step of locating includes the step of adjusting the locations of said at least one ultrasonic receiver unit such that said first and second receipt times are generally equivalent.

22. Method according to claim 21 and wherein said step of locating includes the step of determining said first and said second receipt times.

23. Method according to claim 21 and wherein said step of locating includes the step of using a rocker unit to rockingly press said at least one ultrasonic receiver unit into said interposed medium.

24. Method according to claim 20 and wherein said step of determining includes the step of pulsing said transmission means thereby to transit ultrasonic waves when said first and second receipt times are generally equivalent.

25. Method according to claim 20 and wherein said solid is in vivo bone.

26. Method according to claim 20 and wherein said solid is selected from the group of metal, plastics and wood.

27. Method according to claim 20 and wherein the velocity of said ultrasonic waves through said interposed medium is less than the velocity of said ultrasonic wave through said solid.

28. Method according to claim 20 and wherein said at least one ultrasonic receiver unit is placed onto a surface of said interposed medium generally without any coupling medium.

29. Method according to claim 20 and including the step of transmitting said ultrasonic waves in a wide band pattern and wherein said ultrasonic waves generates longitudinal, surface and transverse waves in said solid.

30. Method according to claim 29 and including the steps of processing signals from said at least one ultrasonic receiver unit and identifying a receipt time of said longitudinal wave.

31. Method according to claim 30 and wherein said step of processing includes the step of identifying receipt times of said surface and transverse waves.

32. Method according to claim 31 and wherein said step of processing includes the step of determining said mechanical properties from said receipt times of said surface and transverse waves.

33. Method according to claim 30 and wherein said step of processing includes the step of determining said mechanical properties from at least said receipt time for said longitudinal wave.

34. A method for determining, through an interposed medium, the mechanical properties of a solid, the method comprising the steps of:
transmitting an ultrasonic wave through said interposed medium and said solid, wherein said solid has a surface;
receiving said ultrasonic wave with at least first and second ultrasonic receiver units; and
locating said ultrasonic receiver units such that a first receipt time of said ultrasonic wave from said surface to said first ultrasonic receiver unit is generally equivalent to a second receipt time from said surface to said second ultrasonic receiver unit, said step of locating including the step of:
using a rocker unit to rockingly press said ultrasonic receiver units into said interposed medium thereby adjusting the locations of said receiver units such that said first and second receipt times are generally equivalent.

* * * * *